US008770038B2

(12) United States Patent
Secq

(10) Patent No.: US 8,770,038 B2
(45) Date of Patent: Jul. 8, 2014

(54) TRIAXIAL CELL FOR THE TESTING OF GEOMATERIALS IN COMPRESSION AND IN SHEAR

(75) Inventor: Jean Secq, Villeneuve d'Ascq (FR)

(73) Assignee: Universite des Sciences et Technologies de Lille, Villeneuve d'Ascq (FR)

( * ) Notice: Subject to any disclaimer, the term of this patent is extended or adjusted under 35 U.S.C. 154(b) by 312 days.

(21) Appl. No.: 13/002,730

(22) PCT Filed: Jul. 7, 2009

(86) PCT No.: PCT/FR2009/000837
§ 371 (c)(1),
(2), (4) Date: Jan. 5, 2011

(87) PCT Pub. No.: WO2010/004136
PCT Pub. Date: Jan. 14, 2010

(65) Prior Publication Data
US 2011/0132099 A1    Jun. 9, 2011

(30) Foreign Application Priority Data

Jul. 7, 2008    (FR) .................................. 08 03850

(51) Int. Cl.
*G01N 3/08*    (2006.01)
(52) U.S. Cl.
USPC .............................................. 73/821; 73/783

(58) Field of Classification Search
USPC ................... 73/845, 860, 856, 783, 841, 846
See application file for complete search history.

(56) References Cited

U.S. PATENT DOCUMENTS

| 3,406,567 | A | * | 10/1968 | Terry ............................... 73/841 |
| 3,975,950 | A | | 8/1976 | Erdei |
| 4,579,003 | A | | 4/1986 | Riley |
| 5,253,518 | A | * | 10/1993 | Steiger et al. .............. 73/152.23 |
| 5,275,056 | A | | 1/1994 | Hamilton |
| 5,435,187 | A | * | 7/1995 | Ewy et al. ........................ 73/856 |

FOREIGN PATENT DOCUMENTS

| EP | 0349422 A | 1/1990 |
| FR | 2663121 A | 12/1991 |
| FR | 2746920 A | 10/1997 |
| WO | 9821558 A | 5/1998 |

* cited by examiner

*Primary Examiner* — Peter Macchiarolo
*Assistant Examiner* — Mohammed Keramet-Amircola
(74) *Attorney, Agent, or Firm* — Young & Thompson

(57) ABSTRACT

The invention relates to a cell for testing geomaterials on cylindrical specimens, of rock, ground or materials manufactured on sampling sites, including at least one piston for subjecting a specimen to a stress directed along the longitudinal axis of the specimen. According to the invention, the cell has, in addition, means for shearing the specimen, capable of cracking the specimen while it is being compressed in said at least one piston.

8 Claims, 2 Drawing Sheets

TRIAXIAL CELL FOR THE TESTING OF GEOMATERIALS IN COMPRESSION AND IN SHEAR

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The invention relates to a cell for testing geomaterials on cylindrical specimens, in particular rock, ground, or materials manufactured on sampling sites. In particular, the cell will enable to subject the specimen at least to a simple compression or still to subject the specimen to a triaxial test.

2. Description of Related Art Including Information Disclosed Under 37 CFR 1.97 and 37 CFR 1.98

In the field of the geomaterials, triaxial cells, such as for example those disclosed in document FR-2.663.121 are known, which enable to subject a cylindrical specimen to different pressure, loading, temperature and draining conditions. The cell and the specimen are to that end fitted with different sensors, such as for example pressure, temperature, displacement sensors.

The triaxial cell generally comprises a cell body with an internal cavity forming a sealed chamber inside which the cylindrical specimen is placed vertically. A controlled pressurising or draining hydraulic circuit is connected to the sealed chamber for subjecting the lateral wall of the specimen to a radial stress to the pressure of a fluid. Quite often, this constraint is applied through an elastic envelope hugging and protecting the lateral wall of the specimen.

In the sealed chamber, a lower plate and an upper plate may be brought closer to and apart from one another for constraining the specimen along its longitudinal axis or conversely for unloading it.

The lower plate may be fixed relative to the stand formed of a lower mount of the cell body, wherein the upper plate is compelled to move under the action of a piston capable of sliding through the upper wall of the body.

During the tests, it is thus possible to subject the specimen to a simple compression or still to a triaxial test, wherein the specimen is compressed along its longitudinal axis and a radial stress is exerted simultaneously on the lateral wall of the specimen, under the action of a fluid. In the case of a triaxial test notably, it is also possible to subject the specimen to draining conditions so as to study its permeability.

For the loading/compression, possibly permeability tests, it may prove interesting to study a cracked specimen.

Today, so as to obtain the cracked specimen, the specimen is broken previously to the testing phase, thereby creating the crack artificially. In practice, the specimen is broken in two and reconstructed in the test cell. It should be noted that the onset of the crack on the specimen is controlled rather poorly.

U.S. Pat. No. 3,406,567 discloses a portable testing device for measuring the shearing load of a cylindrical specimen, snow or ground.

This device comprises a hollow, rigid cylinder for receiving the specimen, as well as a pair of matrices, respectively sliding at the level of the ends of said hollow cylinder. To that end, each matrix, whose section is adjusted to the inside diameter of the hollow cylinder, exhibits a nipple for engaging into a guiding slot of said hollow cylinder.

The contact surface of the matrix with the specimen, semi-circular in section, only extends over half the matrix, wherein the other half has a cavity so as not to touch the specimen on this area. Both matrices are arranged, relative to each other in an offset manner.

One of the lower matrices rests on the stand of the device, wherein the other matrix is mobile relative to this mount by means of a jack for constraining the specimen.

During testing, it is then possible to constrain the specimen until said specimen cracks. the shearing load can be measured especially by analysing the load-time curve.

However, once the specimen has been cracked in two parts, such a device hardly enables control of the relative displacement between both parts.

The aim of the present invention is to remedy the drawbacks aforementioned while offering a test cell enabling to crack the specimen in situ, while restricting the relative displacement of the cracked parts.

Another aim of the present invention is to be able to control the positions of the crack at least at the ends of the specimen.

Another aim of the present invention is to offer a cell at least enabling to subject the specimen to a simple compression test.

Another aim of the present invention is to offer a cell enabling to subject the specimen to a triaxial test.

Another aim of the present invention is to offer a cell for conducting permeability tests on the cracked specimen.

Other aims and advantages of the present invention will appear in the following description which is given only by way of example and without being limited thereto.

BRIEF SUMMARY OF THE INVENTION

The invention relates to a cell for testing geomaterials on cylindrical specimens, in particular rock, ground or materials manufactured on sampling sites, including at least one piston for subjecting a specimen to a stress directed along the longitudinal axis of the specimen. The cell exhibits moreover means for shearing the specimen capable of cracking the specimen when the specimen is compressed by said at least one piston.

Advantageously, said shearing means includes two heterogeneously deformable elements, subjected to the action of said at least one piston, respectively in contact with the bases of the specimen.

BRIEF DESCRIPTION OF THE SEVERAL VIEWS OF THE DRAWINGS

The invention will be understood better when reading the following description accompanied by the appended drawings among which.

DETAILED DESCRIPTION OF THE INVENTION

Figure 1:
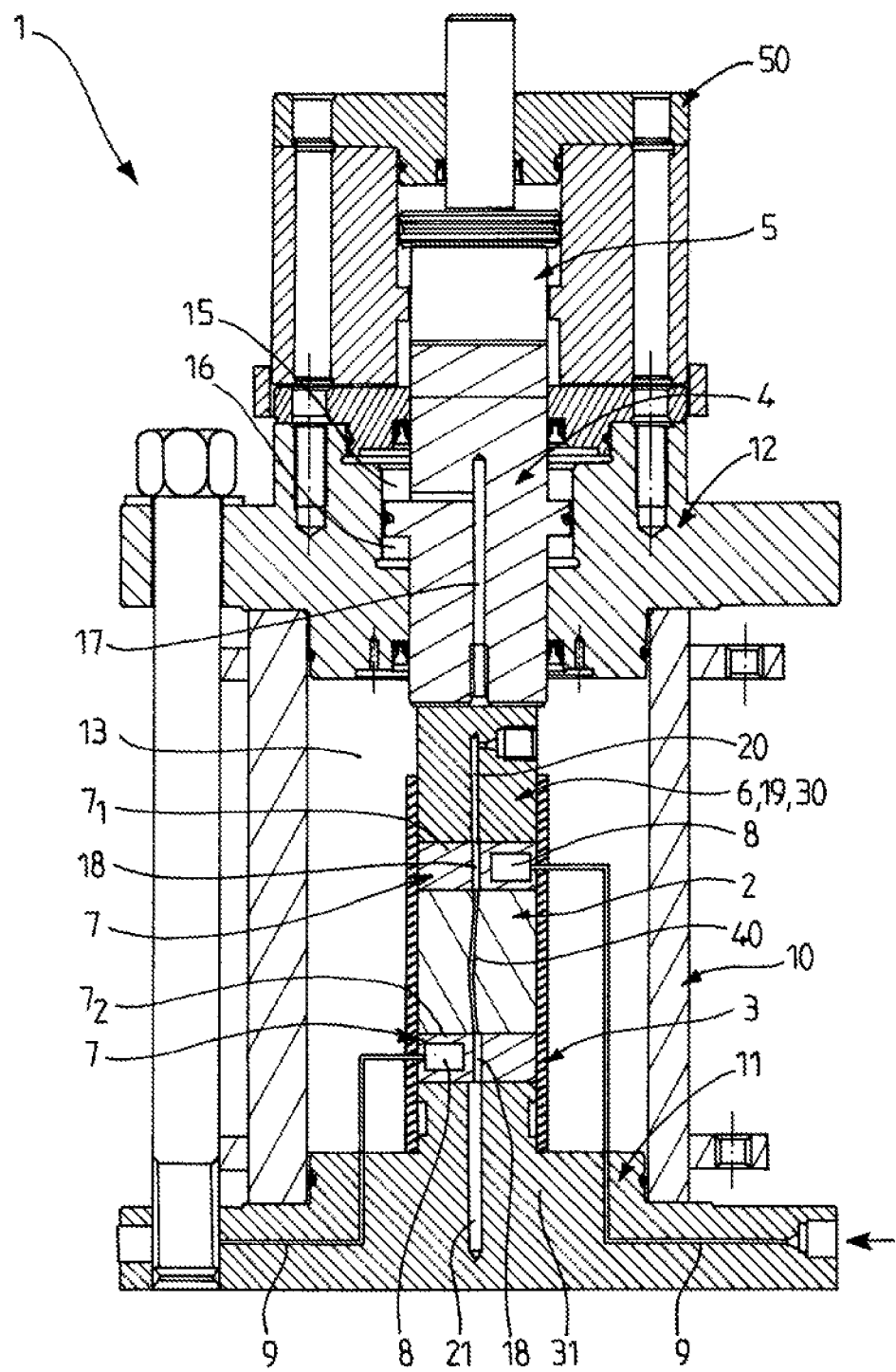
FIG. 1 is a vertical sectional view of a cell according to the invention, in a given embodiment, in particular a polyvalent triaxial test cell.

The invention relates to a cell 1 for testing geomaterials on cylindrical specimens, in particular rock, ground or materials manufactured on sampling sites. It may be a test cell enabling only simple compression tests or still a triaxial test cell.

The cell 1 comprises at least one piston 4, 5 for subjecting a cylindrical specimen 2 to a stress directed along the longitudinal axis of the specimen 2.

The cell 1 includes furthermore means 7 for shearing the specimen capable of cracking the specimen when the specimen 2 is compressed by said at least one piston.

The interest shown by the invention lies in creating the crack when the specimen is compressed by said piston 4, 5.

After cracking the specimen in the case of a triaxial test, it is then possible to conduct permeability tests in the long run, for example, under different confinement pressures, for studying in particular the permeability variability of the break surfaces subjected for example to a slight displacement or still the healing process of certain materials.

The shearing means 7 includes two heterogeneously deformable elements 71, 72 subjected to the action of said at least one piston, respectively in contact with the bases of the specimen.

Advantageously, each heterogeneously deformable element 71, 72 exhibits two halves which deform differently relative to each other when constrained.

Advantageously, according to the examples of the figures especially, both halves of said heterogeneously deformable element, which deform differently, each exhibit a contact surface the specimen. Advantageously, said contact surfaces of both halves may be coplanar at rest.

With reference to FIG. 1, the deformable elements 71, 72 may each exhibit on half said element an internal cavity forming a deformable chamber 8 under the pressure of a fluid. The cell exhibits at least one hydraulic circuit 9 for pressurising said chamber.

Previously to or simultaneously with the compression of the specimen by said at least one cylinder 4, 5, the thickness of the element 71, 72 can for example be increased over half the contact-making surface, by pressurising the deformable chamber 8. Both elements 71, 72 in contact with the upper and lower base of the specimen 2 can be advantageously offset angularly along an axis rotation which is coaxial with the specimen axis.

As illustrated, at rest, the contact surface with the specimen is planar and makes contact with the base of the specimen over all its surface. It is only when the deformable chamber 8 is pressurised and/or that when the piston 4, 5 exerts its longitudinal effort, that the contact surface deforms for shearing the specimen.

Once the specimen has been cracked in two parts, the displacement between the parts is minimal, whereas both cracked parts are held correctly by the elements 71, 72, without any excessive displacement.

We shall note besides that the contact surface of the deformable element 71, 72, which is planar at rest according to the illustrated examples, enables one to facilitate the mounting of the specimen in the test cell, notably the triaxial test cell.

As illustrated on the figures, according to an example the upper deformable member 71 is cylindrical, in contact on the one hand with the upper base of the specimen 2, and on the other hand, with an upper plate 30 itself compelled to move by a piston 4.

The lower deformable member 72 is also cylindrical, in contact on the one hand with lower base of the specimen 2, and on the other hand with a lower plate 31, formed by a fixed mount relative to the stand of the cell.

When the upper 30 and lower 31 plates are brought closer to one another, the deformable elements 71, 72 enable shearing of the specimen along its longitudinal axis.

The compression forms a crack 40 extending longitudinally along the specimen, from one deformable element to the other. During testing, it has been noted that the crack takes its rise at the junction of both regions of the element which deform differently. It is then possible to change the orientation of the break surfaces by rotating a deformable element 71 relative to the other 72.

Figure 2:
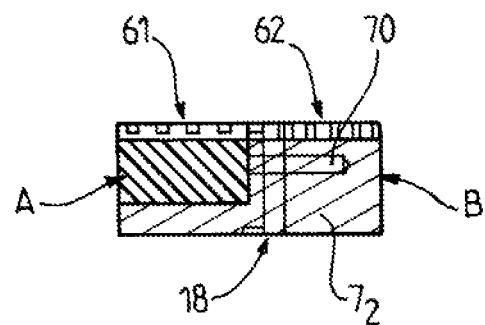
FIG. 2 is a sectional view of a deformable element according to the invention in a given embodiment, substantially formed of two halves in materials of different elasticity moduli.

According to another embodiment, the deformable elements 71, 72 of the cell, illustrated on FIG. 1, can be replaced with two deformable elements as illustrated on FIG. 2.

According to this embodiment illustrated on FIG. 2, each deformable element 71, 72 is substantially formed of two halves A, B in materials of different elasticity moduli.

When the specimen is compressed, the half portion B, for example with lower elasticity, exerts a greater stress relative to the constraint exerted by the half portion A, then of higher coefficient of elasticity. By offsetting angularly the deformable elements 71, 72 in relation to each other, it is then possible to shear the specimen during compression.

According to the non limiting example, the elements are offset by rotation with an axis coaxial to said longitudinal axis of the specimen. The semi-cylindrical half portion A with higher elasticity is made of elastomer, the other half portion B with lower elasticity can be of metal. Both half portions A and B can be assembled by overmoulding techniques. To that end, the metallic part may exhibit a bore 70 for entangling the matter during the moulding process.

As illustrated according to the example of FIG. 2, the deformable member includes a metal cylindrical portion which defines over half its surface the metal surface B, the other half of its surface with smaller thickness forms a shoulder for supporting the elastomer half portion A.

The half portion A is fixed to the part B thanks to overmoulding techniques. At rest, the contact surface of the half portion A and the half portion B are on the same level, i.e. coplanar. It is only when subjected to the axial stress that both half portions deform differently for shearing the specimen.

Figures 3, 4:
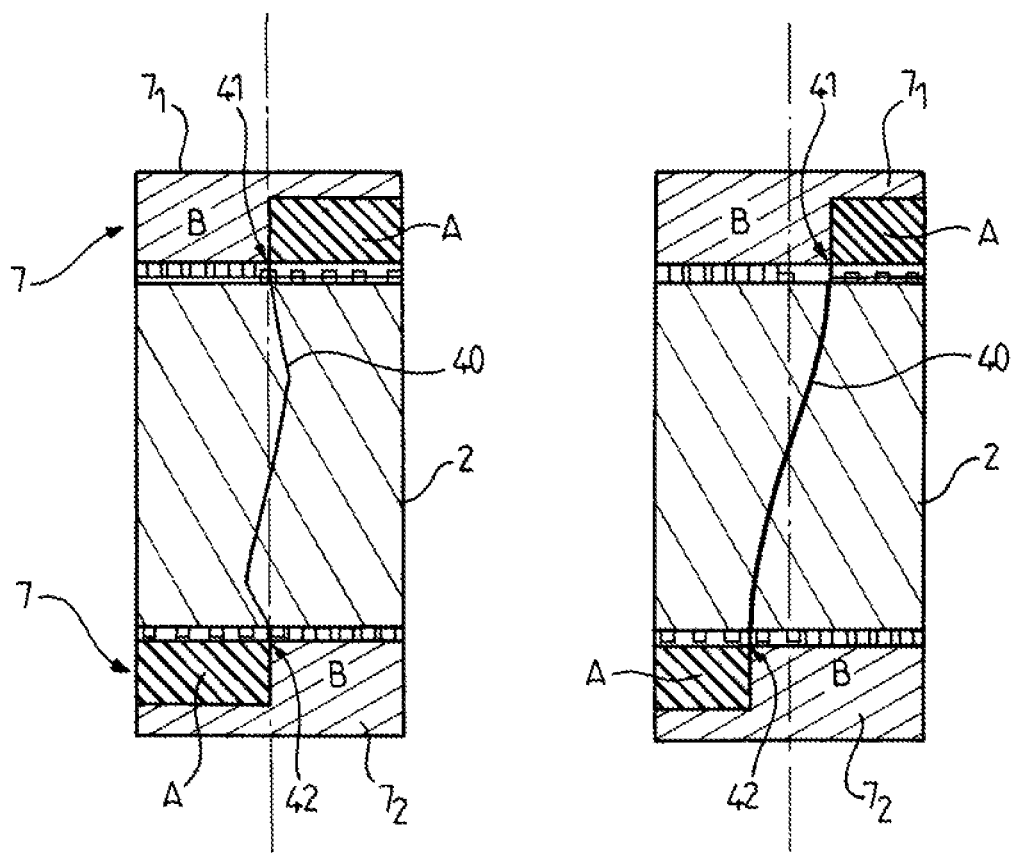
FIG. 3 and FIG. 4 are sectional views of the specimen sandwiched by two deformable elements, as illustrated on FIG. 2, along two relative angular positions between elements.

As illustrated on FIGS. 3 and 4 in particular, it has been noted that the onset of the cracks always lies at the junction 2 of both different deformation regions, especially at the junction between the half portion A and the half portion B. It is then possible to change the orientation of the break surfaces by rotating a deformable element 71 relative to the other 72 with an axis coaxial to the longitudinal axis of the specimen.

If applicable, in order to protect the lateral wall of the specimen, the pressure of the fluid exerts a radial stress through an elastic envelope 3 protecting the specimen 2 by enveloping its sidewall.

The means for subjecting the lateral wall of the specimen substantially include a sealed chamber 13 inside which said specimen connected to a pressurising circuit of said chamber (non illustrated) is placed.

According to the example of FIG. 1, the cell is a self-contained cell and may exhibit:
- a cylindrical cell body 10, closed in a leakproof manner by a lower mount 11 and a lid 12 with an internal cavity forming the sealed chamber 13 inside which the specimen 2 is placed, this chamber is connected to the hydraulic circuit for pressurising said sealed chamber:
- a main piston 4, adjusted for sliding into a first throughbore of the lid 12, having a flange 14 which fits into a second bore 2 of said lid 12, of greater diameter for delineating two chambers 15, 16 therein. The main piston 4 having a self-compensation channel for communicating the fluid of said sealed chamber 13 and of said upper annular chamber 15,
- a module 50, secured removably to the lid 12 exhibiting an auxiliary piston 15 capable of co-operating with the main piston 4, for making said cell autonomous.

The cell may exhibit draining means 6 for subjecting the specimen to the longitudinal passage of a draining fluid.

The draining means may include a channel 20 communicating the fluid of the sealed chamber 13 and the upper base of the specimen 2. This channel extends through the upper plate 30 which then forms a draining mount 6. This channel extends through the upper deformable element 71, in a channel 18 of said element. In the lower section of the specimen, the fluid flows out through a channel 18 of the lower deformable element 72, a channel prolonged by a duct 21 extending into the mount of the cell.

The deformable elements 71, 72 may exhibit, on their surface in contact with the bases of the specimen 2, means for distributing the draining fluid over the whole contact surface. As illustrated on FIG. 2 especially, these means may include at least two grids 61, 62 which respectively cover two surfaces which deform in the same manner when the specimen is compressed.

As illustrated on FIG. 2, one of the grids 61 covers the half portion A with higher modulus of elasticity, especially of elastomer, whereas the other grid 62 covers the other half portion B with lower modulus of elasticity, especially of metal.

It should be noted that these grids may also be employed at the level of the contact surfaces of the elements 71, 72 illustrated on FIG. 1 exhibiting in particular the deformable chamber 8. To that end, one of the grids covers half the surface over which the chamber 8 extends, whereas the other grid covers the surface of the other full half.

Advantageously, sensors may equip the specimen, even the cell to study the shearing behaviour.

These are more particularly:
- one or several sensors for targeting the relative displacement of both shorn parts of the specimen (e.g. LVDT sensors sunk in the deformable elements 71, 72),
- one or several sensors placed along the specimen (e.g. equipped collar) for targeting the opening of the cracking, either during cracking or when both shorn parts are sliding,
- one or several sensors for measuring the pressure in the crack during the tests.

Naturally, other embodiments, understandable to the man of the art, could have been contemplated without departing from the framework of the invention defined in the claims below.

I claim:

1. A cell for testing geomaterials on cylindrical specimens, rock, ground, or materials manufactured on sampling sites, including at least one piston for subjecting a specimen to a load directed along the longitudinal axis of the specimen, said cell exhibiting two elements, subjected to the action of said at least one piston, respectively in contact with the bases of the specimen, each of said two elements is a heterogeneously deformable element, exhibiting two half portions which deform differently relative to one another when constrained, one half of the half portions being made of an elastomer, the other half portion being made of metal, each half having a contact surface with the specimen, wherein the contact surfaces of said two half portions are coplanar at rest, so that when said specimen is compressed by said at least one piston between the said two elements, the specimen is cracked, the crack extending longitudinally along the specimen from one said deformable element to said other deformable element.

2. The cell according to claim 1, in which said deformable elements each exhibit on half said element an internal cavity forming a chamber which is deformable under the pressure of a fluid, said cell having at least one hydraulic circuit for pressurising said chamber.

3. The cell according to claim 1, wherein the deformable elements are offset angularly, in relation to each other, along an axis rotation which is coaxial to said longitudinal axis of the specimen.

4. The cell according to claim 1, wherein said cell is a triaxial cell which exhibits a sealed chamber, which contains said specimen and a circuit for pressurising said sealed chamber, for subjecting the lateral wall of the specimen to the pressure of a fluid.

5. The cell according to claim 4, exhibiting draining means for subjecting the specimen to a longitudinal passage of a draining fluid, said deformable elements exhibiting a channel for the passage of said draining fluid.

6. The cell according to claim 5, in which the deformable elements present, on their surface in contact with the bases of the specimen, at least two grids associated respectively to said both half portions for distributing the draining fluid over the whole contact surface.

7. A method for cracking a specimen and conducting permeability tests in the long run, wherein the steps are implemented in a cell according to claim 4, said method including at least the following steps:
   cracking said specimen by compressing said specimen between said two elements,
   conducting permeability tests by subjecting the lateral wall of the specimen to the pressure of a fluid.

8. The cell according to claim 4, wherein the lateral wall of the specimen is subjected to the pressure of a fluid through an elastic envelope protecting said specimen.

\* \* \* \* \*